(12) United States Patent
Mukherjee et al.

(10) Patent No.: US 9,079,815 B2
(45) Date of Patent: Jul. 14, 2015

(54) PRODUCTION OF A HIGH OCTANE ALKYLATE FROM ETHYLENE AND ISOBUTENE

(75) Inventors: Mitrajit Mukherjee, East Hanover, NJ (US); John F. Young, Hillsborough, NJ (US); James P. Nehlsen, Stroudsburg, PA (US); George D. Suciu, Ridgewood, NJ (US); Kelly Ann Coley, Warren, NJ (US)

(73) Assignee: Exelus Inc, Fairfield, NJ (US)

( * ) Notice: Subject to any disclaimer, the term of this patent is extended or adjusted under 35 U.S.C. 154(b) by 208 days.

(21) Appl. No.: 13/200,723

(22) Filed: Sep. 29, 2011

(65) Prior Publication Data

US 2012/0088948 A1     Apr. 12, 2012

Related U.S. Application Data

(60) Provisional application No. 61/404,597, filed on Oct. 6, 2010.

(51) Int. Cl.
| | |
|---|---|
| C07C 2/58 | (2006.01) |
| C07C 2/56 | (2006.01) |
| B01J 23/89 | (2006.01) |
| B01J 23/96 | (2006.01) |
| B01J 29/74 | (2006.01) |
| B01J 29/76 | (2006.01) |
| B01J 29/90 | (2006.01) |
| B01J 35/00 | (2006.01) |
| B01J 37/04 | (2006.01) |
| C10G 29/20 | (2006.01) |
| C10G 57/00 | (2006.01) |
| B01J 21/12 | (2006.01) |
| B01J 29/08 | (2006.01) |
| B01J 29/78 | (2006.01) |

(52) U.S. Cl.
CPC ............ *C07C 2/58* (2013.01); *B01J 23/892* (2013.01); *B01J 23/96* (2013.01); *B01J 29/7415* (2013.01); *B01J 29/7615* (2013.01); *B01J 29/90* (2013.01); *B01J 35/0006* (2013.01); *B01J 37/04* (2013.01); *C10G 29/205* (2013.01); *C10G 57/005* (2013.01); *B01J 21/12* (2013.01); *B01J 29/087* (2013.01); *B01J 29/7815* (2013.01); *C07C 2521/12* (2013.01); *C07C 2523/42* (2013.01); *C07C 2529/12* (2013.01); *C07C 2529/74* (2013.01); *C07C 2529/76* (2013.01); *C10G 2300/1081* (2013.01); *C10G 2300/1092* (2013.01); *C10G 2400/02* (2013.01)

(58) Field of Classification Search
CPC ..................................... C07C 2/56; C07C 2/58
USPC ..................................................... 585/722, 721
See application file for complete search history.

(56) References Cited

U.S. PATENT DOCUMENTS 3,754,052 A    8/1973 Hoffman et al.
3,761,540 A *  9/1973 Hutson et al. .................. 585/723
(Continued)

OTHER PUBLICATIONS

Goupil et al., Alkylation of Isobutane by ethylene: A Thermodynamic study, 1994, Ind. Eng. Chem. Res., vol. 33, pp. 712-717.*

*Primary Examiner* — In Suk Bullock
*Assistant Examiner* — Youngsul Jeong
(74) *Attorney, Agent, or Firm* — Raymond J. Lillie (57) ABSTRACT

A method of producing a high octane alkylate from ethylene and isobutane by reacting ethylene and isobutane under catalytic conversion conditions. The ethylene and isobutane are contacted with a first catalytic material comprising a dimerization catalyst (i.e, for dimerizing ethylene) and a second catalytic material comprising an alkylation catalyst. The first and second catalytic materials are separate and distinct from each other. A high octane alkylate is recovered as a result of reacting the ethylene and isobutane in the presence of the first and second catalytic materials.

17 Claims, 3 Drawing Sheets

(56) References Cited

U.S. PATENT DOCUMENTS

| | | |
|---|---|---|
| 3,795,714 A | 3/1974 | Pickert et al. |
| 3,893,942 A * | 7/1975 | Yang .......................... 585/722 |
| 4,211,885 A | 7/1980 | Banks |
| 5,073,665 A | 12/1991 | Child et al. |
| 5,449,849 A * | 9/1995 | DiGuiseppi et al. .......... 585/510 |
| 6,025,534 A * | 2/2000 | Valente et al. ................ 585/529 |
| 6,040,259 A * | 3/2000 | Mohr et al. ..................... 502/67 |
| 7,550,644 B2 * | 6/2009 | Pfefferle ........................ 585/720 |
| 2004/0158113 A1* | 8/2004 | Srinivas et al. ............... 585/721 |

* cited by examiner

PRODUCTION OF A HIGH OCTANE ALKYLATE FROM ETHYLENE AND ISOBUTENE

This application claims priority based on Provisional Application Ser. No. 61/404,597, filed Oct. 6, 2010, the contents of which are incorporated by reference in their entirety.

This invention relates to the production of a high octane alkylate from a feed comprising ethylene and isobutane. More particularly, this invention relates to the production of a high octane alkylate from ethylene and isobutane by reacting ethylene and isobutane under catalytic conversion conditions in the presence of a first catalytic material which includes a dimerization catalyst, and a material which promotes regeneration of the dimerization catalyst, and a second catalytic material which includes an alkylation catalyst, wherein the first and second catalytic materials are separate and distinct from each other.

Fluid catalytic cracking, or FCC, is at the heart of every modern refinery, whereby heavy petroleum components are converted into high-value fuels. The FCC operation, as well as other common cracking processes, invariably makes a range of products, from light gases to heavy fuel oil. Included in this range are light paraffins and olefins in the range of $C_2$ (ethane, ethylene) to $C_4$ (butane, isobutane, butenes, isobutylene). Typically, a refiner will combine chemically the $C_4$ olefins (and possibly $C_3$ and $C_5$ olefins as well) with the isobutane in a process called alkylation. The product from this process is called alkylate.

Alkylate is the cleanest gasoline blending stream produced in refineries and is an ideal clean fuel component because it has a high octane rating, low vapor pressure, and low toxicity. Alkylate has been blended into gasoline for decades to improve octane and thus the antiknock properties of gasoline. In addition, strict state and federal limitations on the formulation and physical properties of gasoline makes alkylate one of the most important and valuable blendstocks of the gasoline pool.

Currently, large scale production of alkylate is produced by a process known as isoparaffin alkylation. Commercially, isoparaffin alkylation is a liquid acid catalyzed reaction that combines isobutane with alkenes such as propylene, butenes, and amylenes ($C_3$-$C_5$ olefins). For this process, refiners employ either hydrofluoric acid (HF) or sulfuric acid ($H_2SO_4$) as the liquid alkylation catalyst.

Ethylene ($C_2$ olefin) is another major component produced in the FCC unit. Although the liquid acid catalysts used in all commercial alkylation units are quite effective in activating the $C_3$-$C_5$ olefins, they cannot activate ethylene. Instead ethylene forms stable ethyl ethers with the acids in these units, thereby providing an inert and useless mixture. (Nivarty, et al., *Microporous and Mesoporous Materials*, Vol. 35-36, pages 75-87 (2000)). Consequently, no commercial alkylation units are capable of alkylating ethylene.

In alkylation, protonation of the olefin is a vital initiation step (Corma, et al., *Trends Catal. Rev.-Sci. Eng.*, Vol. 35, pg. 483 (1993), and thus activation of the olefin greatly depends on the stability of the carbocation generated. Inherently, ethylene is less reactive compared to butene; protonation of either carbon atom in ethylene results in the formation of an unstable primary carbocation, whereas protonation of butene forms a more-stable secondary carbocation.

Butene can be protonated easily during conventional alkylation by Brønsted acids, such as the conventional liquid acid catalysts. In contrast, Friedel-Crafts type catalysts such as $BF_3$ and chlorided alumina are needed to activate ethylene for alkylation (Goupil, et al., *Catalysis Letters*, Vol. 31, pages 121-131 (1995); Hoffman, U.S. Pat. No. 3,873,634). The most active catalysts for isoparaffin alkylation with ethylene are mixtures of Lewis acids and protic mineral acids, such as HCl and $AlCl_3$, because such blends have Lewis sites capable of activating ethylene and the requisite Brønsted sites that promote the subsequent hybrid shift reactions (Olah, et al., *Hydrocarbon Chemistry*, $2^{nd}$ Edition, Wiley Interscience, page 632 (1995)). A related catalyst, an ionic liquid with an aluminum chloride anion, was used in U.S. Pat. No. 7,432,408 to alkylate isopentane with ethylene.

These catalysts, however, are sensitive to trace water, deactivate readily, and corrode equipment. Therefore, they are not suitable for a cost-effective refinery process and have not been employed commercially for this use.

Zeolites possess both Brønsted and Lewis acid sites; however, these catalysts do not exhibit high activity for ethylene alkylation. For example, it was reported that zeolite Beta displayed stable ethylene conversion of only 40% for ten hours but gave complete conversion for butene (Nivarthy, et al.) under the same conditions. It also has been calculated in other zeolitic systems that the activation barrier for protonation of ethylene can be quite high (23-30 kcal/mol) (Namuangruk, et al., *Chemphys. Chem.*, Vol. 6, pages 1333-1339 (2005); Svelle, et al., *J. Physical Chemistry*, Vol. 108, pages 2953-2962 (2004)). As a result of this low activity, known solid acid catalysts also are unsuitable for alkylating directly with ethylene in a commercial process, as they would require impractically large quantities of catalyst.

Ethylene can be converted into butene by dimerization, whereby two ethylene molecules are combined into a single butene molecule. Dimerization of ethylene to butene is practiced commercially in the Axens Alphabutol process, for example. Such commercial processes require highly selective homogeneous catalysts, such as those disclosed in U.S. Pat. No. 5,162,595, and are limited to relatively pure streams of ethylene. Heterogeneous catalysts for ethylene oligomerization are not selective for butenes and provide for the production of less desired higher olefins.

One known alternative used to circumvent the problem of low ethylene reactivity (http://www.icis.com/Articles/1999/05/31/81473/the-ethalk-route-to-high-octane-alkylate.html) is to incorporate an ethylene dimerization function into an alkylation catalyst. With this catalyst, the ethylene first is dimerized into butenes, which then undergo conventional alkylation with isobutane. Butenes are much more reactive for alkylation than ethylene, resulting in a higher overall reaction rate. This, however, still requires a suitable alkylation catalyst, and the addition of a dimerization function to the alkylation catalyst prevents the combined catalyst from being regenerated due to the formation of difficult-to-remove ethylene oligomers and coke.

The problem with this approach is that the dimerization sites within the alkylation catalyst become deactivated with use by a type of coke that cannot be removed except under very harsh regeneration conditions. The only method suitable for regenerating the dimerization sites on such a catalyst is first to oxidize the coke with an oxygen-containing stream such as air, and then hydrogenate any remaining coke using a hydrogen-containing stream. Both steps occur at elevated (250° C.) temperatures. Such regeneration schemes are not practical in industrial operation due to the hazards of introducing oxygen to a hydrocarbon process and the need to purge the system frequently as it is changed from hydrocarbon-based to oxygen-based.

The present invention is directed to producing a high octane alkylate from either concentrated or diluted streams of ethylene, in contrast to conventional processes that are capable of employing only concentrated ethylene streams.

In accordance with an aspect of the present invention, there is provided a method of producing a high octane alkylate from ethylene and isobutane. The method comprises reacting ethylene and isobutane under catalytic conversion conditions. The ethylene and isobutane are contacted with a first catalytic material and a second catalytic material. The first catalytic material comprises a dimerization catalyst and a material which promotes regeneration of the dimerization catalyst. The second catalytic material comprises an alkylation catalyst. The first catalytic material and the second catalytic material are separate and distinct from each other. Subsequent to the reacting of the ethylene and isobutane, a high octane alkylate is recovered.

The term, "separate and distinct from each other," with respect to the first and second catalytic materials, as used herein, means that the first and second catalytic materials are two independent and physically separate materials. Although, in non-limiting embodiments of the present invention, the first and second catalytic materials may be admixed physically with each other, e.g., wherein particles or pellets of the first catalytic material and particles or pellets of the second catalytic material are contained in the same catalyst bed, or the first and second catalytic materials may be contained in the same particle or pellet, the first and second catalytic materials retain their separate identities.

The first catalytic material, as noted hereinabove, comprises a dimerization catalyst and a material which promotes regeneration of the dimerization catalyst. The dimerization catalyst catalyzes the dimerization of ethylene to butene, which then is reacted with isobutane to produce a high octane alkylate. In a non-limiting embodiment, the dimerization catalyst comprises a metal and a support for the metal. Metals which may be employed in the dimerization catalyst include, but are not limited to, nickel, palladium, chromium, vanadium, iron, cobalt, ruthenium, rhodium, copper, silver, rhenium, molybdenum, tungsten, and manganese. Supports which may be employed include, but are not limited to, zeolites, alumina, silica, carbon, titania, zirconia, silica/alumina, and mesoporous silicas.

In a non-limiting embodiment, the dimerization catalyst is made by depositing or impregnating salts of the metal onto the support. In a non-limiting embodiment, the metal is deposited or impregnated onto the support in an amount of about 0.1 wt. % to about 10 wt. %, based on the weight of the support. The catalyst then is dried and calcined in air or nitrogen, thereby anchoring the metal to the support.

Although the scope of the present invention is not to be limited to any theoretical reasoning, it is believed that the activity of the dimerization catalyst is created by the interaction of the metal and the support. In a non-limiting embodiment, dimerization catalysts which may be employed include, but are not limited to, nickel supported on dealuminated zeolite Y; nickel supported on impregnated silica/alumina; nickel supported on the aluminum exchanged mesoporous zeolite AlMCM-41; nickel supported on zeolite ZSM-5; bis (imino) pyridyl iron (II) supported on silica; iron (II) tridentate di (imino) supported on silica gel; manganese, chromium, and/or vanadium with modified methylaluminoxane ligands; nickel, cobalt, palladium, platinum, or iron supported on silica activated with modified methylaluminoxane ligands; and chromium supported on silica gel with aluminum reagents.

The dimerization catalyst also includes a material which promotes regeneration of the dimerization catalyst. In a non-limiting embodiment, the material which promotes regeneration of the dimerization catalyst is a hydrogenation catalyst. Hydrogenation catalysts which may be employed include, but are not limited to, platinum, nickel, and palladium. In a non-limiting embodiment, the hydrogenation catalyst is platinum. In another non-limiting embodiment, the hydrogenation catalyst is palladium. In another non-limiting embodiment, the hydrogenation catalyst is nickel.

The alkylation catalyst in general is a catalyst which exhibits at least some activity for the alkylation of isobutane with butenes (i.e., formed as a result of the dimerization of ethylene). In a non-limiting embodiment, alkylation catalysts which may be employed include, but are not limited to, zeolites, sulfated zirconia, tungstated zirconia, chlorided alumina, aluminum chloride ($AlCl_3$), silicon-aluminum phosphates, titaniosilicates (including VTM zeolite), polyphosphoric acid (including solid phosphoric acid, or SPA, catalysts, which are made by reacting phosphoric acid with diatomaceous earth), polytungstic acid, and supported liquid acids such as triflic acid on silica, sulfuric acid on silica, hydrogen fluoride on carbon, antimony fluoride on silica, and aluminum chloride ($AlCl_3$) on alumina ($Al_2O_3$).

In a non-limiting embodiment, the alkylation catalyst is a zeolite. Zeolites which may be employed include, but are not limited to, zeolite Beta; BEA* zeolites; MCM zeolites; faujasites including zeolite X, zeolite Y (including rare earth-exchanged zeolite X and zeolite Y), and USY zeolites; LTL zeolites; mordenite; MFI zeolites, including ZSM-5; EMT zeolites; LTA zeolites; ITW zeolites, ITQ zeolites, and SFO zeolites.

As noted hereinabove, ethylene and isobutane are reacted under catalytic conversion conditions and are contacted with the first and second catalytic materials hereinabove described to produce a high octane alkylate. In a non-limiting embodiment, the feed, in addition to ethylene and isobutane, also may include paraffins (e.g., methane, ethane, propane, butane, etc.) and olefins (e.g., propylene, butenes, pentenes, etc.). The feed is reacted over the catalytic materials to produce alkylate. If the feed includes olefins other than ethylene, such olefins also may be reacted to produce alkylate. In addition, isoparaffins other than isobutane (e.g., isopentane), if present, also may be reacted to form alkylate.

The reaction may be conducted in the liquid phase, a mixed gas-liquid phase, or the gas phase. In a non-limiting embodiment, the reaction is conducted in the liquid phase or in a mixed phase in which the ethylene-containing stream is combined with a liquid isobutane-containing stream to make a two-phase feed stream. The composition of each phase is determined by the vapor-liquid equilibrium of the resulting mixture at the temperature and pressure used.

The ethylene and isobutane are reacted under conditions which produce a high octane alkylate. In a non-limiting embodiment, the ethylene and isobutane are reacted at a temperature of from about 60° to about 150° C. In another non-limiting embodiment, the ethylene and isobutane are reacted at a temperature of about 75° C.

In another non-limiting embodiment, the ethylene and isobutane are reacted at a pressure of up to about 500 psig. In yet another non-limiting embodiment, the ethylene and isobutane are reacted at a pressure of from about 300 psig to about 400 psig.

In a further non-limiting embodiment, the ethylene and isobutane are reacted at a molar ratio of isobutane to ethylene of from about 5 to about 15. In another non-limiting embodiment, the ethylene and isobutane are reacted at a molar ratio of from about 8 to about 12.

In a non-limiting embodiment, the method of the present invention further comprises regenerating the first catalytic material. In a further non-limiting embodiment, the regeneration of the first catalytic material comprises contacting the first catalytic material with hydrogen. In yet another non-limiting embodiment, the first catalytic material is contacted with hydrogen at a temperature of from about 250° C. about 350° C.

Although the scope of this embodiment of the present invention is not to be limited to any theoretical reasoning, it is believed that the hydrogen reacts with ethylene oligomers (eg., hexene, octene) which may have formed on the first catalytic material in the presence of the hydrogenation catalyst contained in the first catalytic material, whereby the oligomers become saturated, thereby enabling the saturated oligomers to be desorbed thermally from the first catalytic material, thereby providing for the regeneration of the dimerization catalyst contained in the first catalytic material.

As noted hereinabove, the first and second catalytic materials are separate and distinct from each other. By keeping the first and second catalytic materials separate and distinct from each other, the formation of hard coke on the alkylation catalyst included in the second catalytic material is prevented.

More particularly, the strong acid sites which are present on the alkylation catalyst do not contribute to the formation of hard coke on both the dimerization catalyst and the alkylation catalyst. By keeping the first and second materials separate and distinct from each other, the first and second catalytic materials are prevented from interacting with each other undesirably, thereby preventing the formation of coke which would make regeneration of the first and second catalytic materials more difficult.

The first and second catalytic materials may be combined in a single reactor or, may be contained in separate reactors. In yet another alternative non-binding embodiment, there is provided a plurality (i.e., three or more) reactors, in which reactors containing the first and second catalytic materials are arranged in an alternating series.

In a non-limiting embodiment, particles or pellets of the first catalytic material and particles or pellets of the second catalytic material are combined in a single reactor. In one non-limiting embodiment, when particles or pellets of the first catalytic material are combined with particles or pellets of the second catalytic material in a single reactor, the particles or pellets of the first and second catalytic materials are combined at a weight ratio of the first catalytic material to the second catalytic material of from about 1:10 to about 10:1. In another non-limiting embodiment, the particles or pellets of the first and second catalytic materials are combined at a weight ratio of the first catalytic material to the second catalytic material of from about 1:5 to about 5:1.

In another non-limiting embodiment, the first catalytic material and the second catalytic material are mixed and combined physically into particles or pellets, whereby each of such particles or pellets includes the first catalytic material and the second catalytic material. In such particles, or pellets, the first catalytic material is not contained within the second catalytic material or absorbed on the surface of the second catalytic material and vice versa. In one non-limiting embodiment, when the first and second catalytic materials are mixed and combined physically into particles or pellets, the first and second catalytic materials are mixed and combined at a weight ratio of the first catalytic material to the second catalytic material of from about 1:10 to about 10:1. In another non-limiting embodiment, the first and second catalytic materials are mixed and combined at a weight ratio of the first catalytic material to the second catalytic material of from about 1:5 to 5:1.

Although the scope of the above embodiments is not intended to be limited to any theoretical reasoning, the physical mixing of the two catalytic materials provides for rapid consumption of butenes formed on the dimerization catalyst through the alkylation of isobutane with the butenes in the presence of the alkylation catalyst. This enhances the quality and yield of alkylate formed by minimizing the production of higher oligomers of ethylene (e.g., hexenes, octenes). Such physical mixing of the first and second catalytic materials also limits the dimerization activity, which is highly exothermic, thereby reducing "hot spots" in the catalyst bed. In addition, the relative amount of ethylene dimerization activity and alkylation activity can be controlled by adjusting the amounts of each of the first and second catalytic materials.

Thus, the present invention enables one to react as much ethylene as possible, produces a high octane alkylate that is almost identical to that produced when using butenes as the initial olefin, and employs a regenerable catalyst that requires only a single regeneration step.

The invention now will be described with respect to the drawings, wherein.

EXAMPLES

The invention now will be described with respect to the following examples. It is to be understood, however, that the scope of the present invention is not intended to be limited thereby.

Example 1

This example demonstrates that adding a dimerization catalyst to a known alkylation catalyst results in a significant improvement in performance when using ethylene as the olefin.

An alkylation catalyst was prepared by converting zeolite Beta into its acidic form through exchange with a 0.5 M ammonium nitrate solution, followed by drying and calcination, using techniques well established in the art. To one portion of this material a dimerization catalyst in the form of tetraamine palladium (II) nitrate was added to achieve a loading of 0.1 wt % Pd in the finished catalyst. The Pd salt was added via conventional wet impregnation procedures that included dissolving the desired amount of salt in distilled water, adding the solution to the dry catalyst, allowing the solution to remain in the catalyst for a period of 4 hours, removing the solvent (water) through evaporation, and then calcining in air to decompose the salt. Each catalyst was activated in the reactor prior to catalyst testing by passing hydrogen over the catalyst bed at 350° C.

Two gram samples of each of the Pd-impregnated and untreated alkylation catalyst were tested for ethylene alkylation activity under identical conditions. A feed of ethylene in isobutane at a 12 to 1 isobutane to ethylene molar ratio was contacted with a fixed bed of the catalyst in a once-through, continuous flow reactor system. The feed flow rate was at 1.2 $hr^{-1}$ weight hourly space velocity. The reaction temperature was 80° C. and the pressure was 400 psig.

Figure 1:
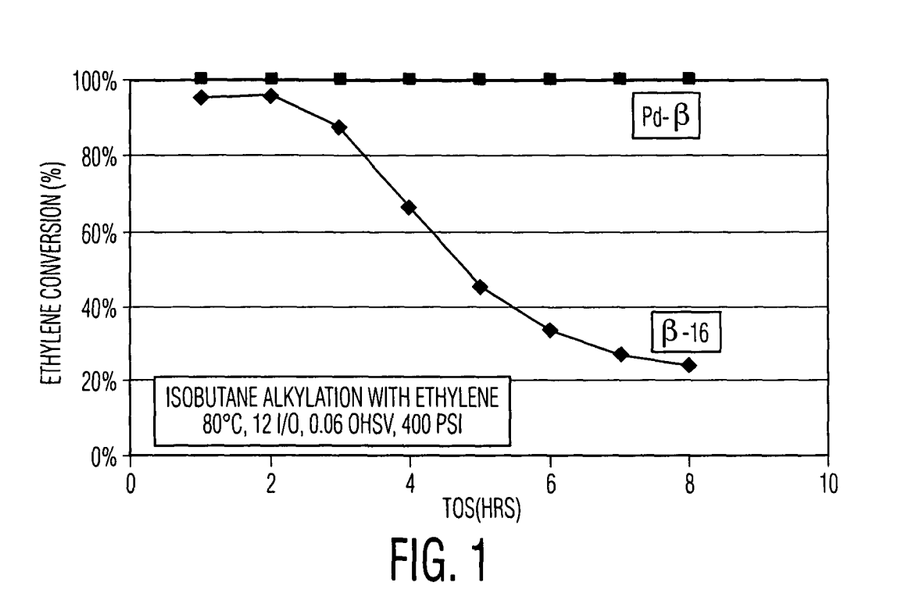
FIG. 1 is a graph of time on stream (TOS) versus percent ethylene conversion, wherein ethylene is reacted with isobutane in the presence of an untreated zeolite Beta catalyst or a zeolite Beta catalyst impregnated with palladium.

The results of this test are shown in FIG. 1. While the untreated catalyst lost activity for ethylene alkylation rapidly, the catalyst including the Pd dimerization catalyst exhibited full ethylene conversion for the duration of the test. Furthermore, the fraction of the alkylate present as desirable octane ($C_8$) isomers increased from 26% with the untreated catalyst to 60% with the Pd-treated catalyst. The alkylate produced by the Pd-treated catalyst had a research octane number (RON) of 90.

Example 2

Figure 2:
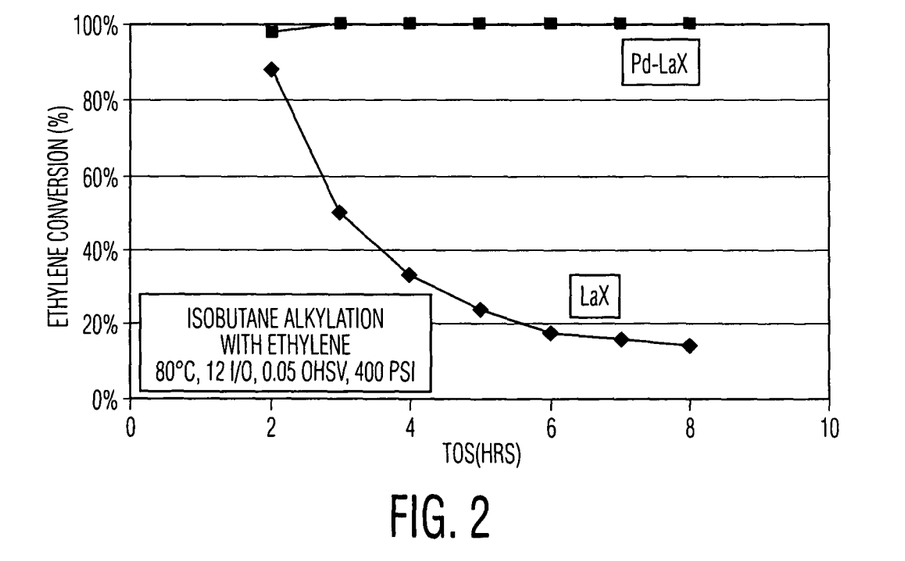
FIG. 2 is a graph of time on stream (TOS) versus percent ethylene conversion, wherein ethylene is reacted with isobutane in the presence of an untreated lanthanum-exchanged zeolite X catalyst or a lanthanum-exchanged zeolite X catalyst impregnated with palladium.

The procedure of Example 1 was repeated except that a La-exchanged zeolite X was used as the parent alkylation catalyst. The catalyst was tested under conditions identical to those in Example 1. The results of this test are shown in FIG. 2. Again, the Pd-containing catalyst exhibits significantly higher activity for ethylene alkylation than the parent material. The fraction of the alkylate present as the desirable octane ($C_8$) isomers increased from 70% with the untreated catalyst to 90% with the Pd-treated catalyst. The alkylate produced by the Pd-treated catalyst had a research octane number (RON) of 97.5.

Example 3

The procedure of Example 1 was repeated except that the alkylation catalyst was exchanged with an aqueous solution of 0.2 M nickel nitrate in lieu of the Pd salt impregnation. The exchanged catalyst was washed with distilled water and dried, and subsequently calcined. The catalyst had a Ni loading of 5 wt %. The Ni-exchanged catalyst was activated and tested in the same manner as Example 1. The results of this test are given in FIG. 3.

Figure 3:
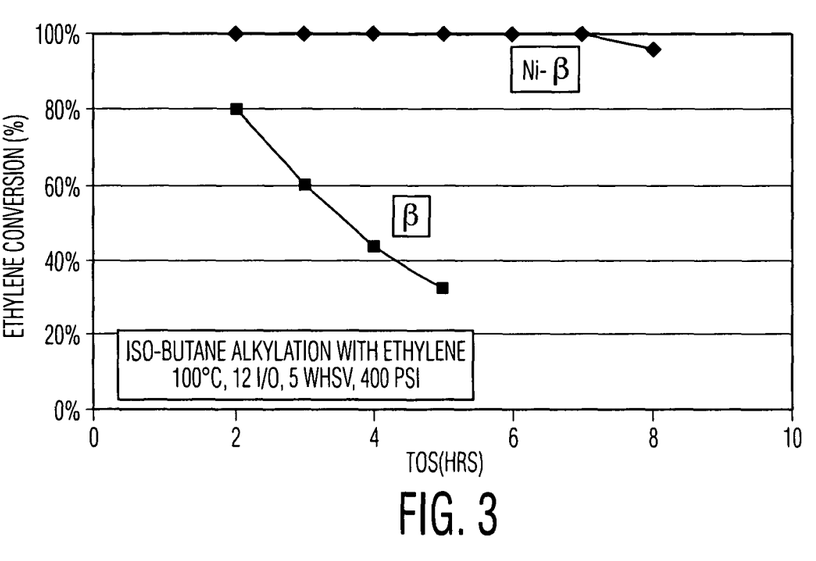
FIG. 3 is a graph of time on stream (TOS) versus percent ethylene conversion, wherein ethylene is reacted with isobutane in the presence of an untreated zeolite Beta catalyst or a zeolite Beta catalyst impregnated with nickel.

As shown in FIG. 3, the nickel-containing catalyst exhibits the same increase in activity as the catalysts containing Pd, which shows clearly that any metal that catalyzes ethylene dimerization may be employed in the present invention. The benefit of having nickel or other base metals is their substantially lower cost compared to a precious metal such as palladium.

Example 4

Figure 4:
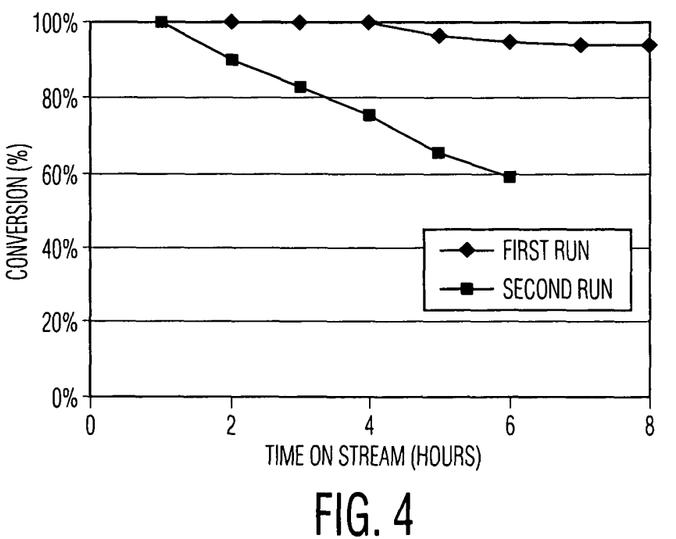
FIG. 4 is a graph of time on stream (TOS) versus percent ethylene conversion, for the first and second reaction runs wherein ethylene is reacted with isobutane in the presence of a zeolite Beta catalyst impregnated with nickel.

Although the catalysts shown in the prior examples are active, they are not able to be regenerated without the undesirable use of an oxidation step. In this example, a common regeneration material, Pt, is added to a fresh sample of the Ni-zeolite Beta catalyst from Example 3. The catalyst is used in the reaction of ethylene and isobutane at a temperature of 75° C., a pressure of 400 psig, an olefin space velocity of 0.20 $hr^{-1}$, and a feed isobutane/ethylene ratio of 12 mol/mol. After 8 hours, the run is stopped and the catalyst is regenerated by heating to 400° C. under flowing hydrogen for 3 hours. The run is then repeated. As shown in FIG. 4, full activity is not restored to the catalyst.

Example 5

Figure 5:
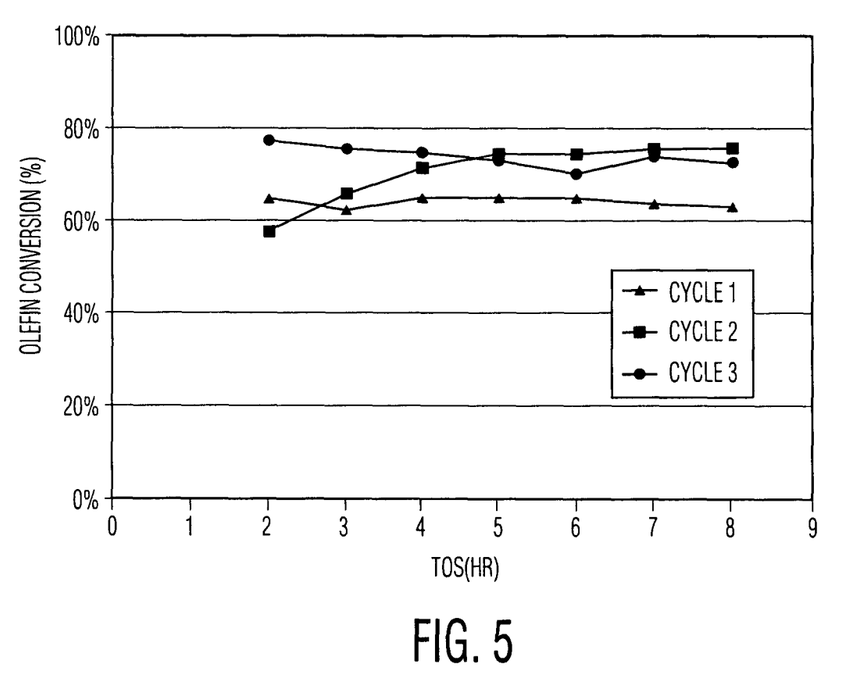
FIG. 5 is a graph of time on stream (TOS) versus percent olefin conversion, wherein ethylene is reacted with isobutane in the presence of separate dimerization and alkylation catalysts.

A dimerization catalyst is made by impregnating 1 wt. % Ni onto a support of silica-alumina. 0.1 wt. % Pt is also added as a hydrogenation catalyst. A separate alkylation catalyst is prepared by adding 0.1 wt. % Pt to zeolite Beta. The two catalysts are mixed physically in a reactor. The mixed catalysts are used for the alkylation of isobutane with ethylene under the same conditions as in Example 4. As in Example 4, the run is stopped after 8 hours, and the catalyst is regenerated by heating to 400° C. under flowing hydrogen for 3 hours. The run was then repeated twice more. The results, shown in FIG. 5, demonstrate that full catalyst activity is restored after each cycle.

The disclosures of all patents and publications (including published patent applications) hereby are incorporated by reference to the same extent as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed:

1. A method of producing a high octane alkylate from ethylene and isobutane, comprising:
    (a) reacting a feed comprising ethylene and isobutane, wherein ethylene is the only olefin contained in said feed, under catalytic conversion conditions, and wherein said ethylene and isobutane are contacted with (i) a first catalytic material comprising a dimerization catalyst and a material which promotes regeneration of said dimerization catalyst and (ii) a second catalytic material comprising an alkylation catalyst wherein said first catalytic material and said second catalytic material are separate and distinct from each other, and wherein said first catalytic material and said second catalytic material have been combined physically into particles or pellets whereby each of said particles or pellets contains said first catalytic material and said second catalytic material; and
    (b) recovering a high octane alkylate from step (a).

2. The method of claim 1 wherein said material which promotes regeneration of said dimerization catalyst is a hydrogenation catalyst.

3. The method of claim 2 wherein said hydrogenation catalyst is selected from the group consisting of platinum, nickel, and palladium.

4. The method of claim 3 wherein said hydrogenation catalyst is platinum.

5. The method of claim 3 wherein said hydrogenation catalyst is palladium.

6. The method of claim 3 wherein said hydrogenation catalyst is nickel.

7. The method of claim 1 wherein said ethylene and said isobutane are reacted at a temperature of from about 60° C. to about 150° C.

8. The method of claim 1 wherein said ethylene and said isobutane are reacted at a temperature of about 75° C.

9. The method of claim 1 wherein said ethylene and said isobutane are reacted at a pressure of up to about 500 psig.

10. The method of claim 9 wherein said ethylene and said isobutane are reacted at a pressure of from about 300 psig to about 400 psig.

11. The method of claim 1 wherein said ethylene and said isobutane are reacted at a molar ratio of isobutane to ethylene of from about 5 to about 15.

12. The method of claim 11 wherein said ethylene and said isobutane are reacted at a molar ratio of isobutane to ethylene of from about 8 to about 12.

13. The method of claim 2, and further comprising:
   (c) regenerating said first catalytic material.

14. The method of claim 13 wherein said regenerating of said first catalytic material comprises contacting said first catalytic material with hydrogen.

15. The method of claim 14 wherein said first catalytic material is contacted with hydrogen at a temperature of from about 250° C. to about 350° C.

16. The method of claim 1 wherein said first catalytic material and said second catalytic material are combined physically into particles or pellets at a weight ratio of said first catalytic material to said second catalytic material of from about 1:10 to about 10:1.

17. The method of claim 16 wherein said first catalytic material and said second catalytic material are combined into particles or pellets at a weight ratio of said first catalytic material to said second catalytic material of from about 1:5 to about 5:1.

* * * * *

UNITED STATES PATENT AND TRADEMARK OFFICE
CERTIFICATE OF CORRECTION

PATENT NO. : 9,079,815 B2
APPLICATION NO. : 13/200723
DATED : July 14, 2015
INVENTOR(S) : Mukherjee et al.

It is certified that error appears in the above-identified patent and that said Letters Patent is hereby corrected as shown below:

In the Claims

Column 8, lines 31-48

Claim 1 of the above-identified patent is corrected such that it reads as follows:

1. A method of producing a high octane alkylate from ethylene and isobutane, comprising:

(a) reacting a feed comprising ethylene and isobutane, wherein ethylene is the only olefin contained in said feed, under catalytic conversion conditions, and wherein said ethylene and isobutane are contacted with (i) a first catalytic material comprising a dimerization catalyst and a material which promotes regeneration of said dimerization catalyst and (ii) a second catalytic material comprising an alkylation catalyst wherein said first catalytic material and said second catalytic material are separate and distinct from each other, and wherein said first catalytic material and said second catalytic material have been combined physically into particles or pellets whereby each of said particles or pellets contains said first catalytic material and said second catalytic material; and (b) recovering a high octane alkylate from step (a), wherein said dimerization catalyst comprises a metal and a support for said metal, said metal is selected from the group consisting of nickel, palladium, platinum, chromium, vanadium, iron, cobalt, ruthenium, rhodium, copper, silver, rhenium, molybdenum, tungsten, and manganese, said support for said metal is silica-alumina, and said alkylation catalyst is a zeolite.

Signed and Sealed this
First Day of December, 2015

Michelle K. Lee
*Director of the United States Patent and Trademark Office*